United States Patent [19]

Pavlo et al.

[11] 4,387,873

[45] Jun. 14, 1983

[54] DEVICE FOR SUSPENSION OF A SOLUTION CONTAINER

[75] Inventors: John A. Pavlo, Hanover Park; Ronald C. Stauber, Hawthorne Woods, both of Ill.

[73] Assignee: Baxter Travenol Laboratories, Inc., Deerfield, Ill.

[21] Appl. No.: 244,188

[22] Filed: Mar. 16, 1981

[51] Int. Cl.³ ............................. E04G 5/06; F16L 3/08
[52] U.S. Cl. ................................ 248/226.4; 211/113; 248/215; 248/311.2
[58] Field of Search ............ 248/214, 215, 318, 311.2, 248/309 R, 226.4, 311.3; 24/31 V, 304, 306; 211/113, 71

[56] References Cited

U.S. PATENT DOCUMENTS

| 417,102 | 12/1889 | Sims | 248/214 |
|---|---|---|---|
| 1,902,241 | 3/1933 | Jones | 248/214 X |
| 2,460,193 | 1/1949 | Raudenkolb | 248/214 |
| 2,843,196 | 7/1958 | Schauer | 248/226.4 X |
| 3,327,419 | 6/1967 | Stanos | 248/205 R UX |
| 3,638,284 | 2/1972 | Baker | 24/306 |
| 3,994,048 | 11/1976 | Rosenthal | 248/306 |
| 4,247,070 | 1/1981 | Dirksing | 248/215 X |

Primary Examiner—J. Franklin Foss
Attorney, Agent, or Firm—Paul C. Flattery; Thomas R. Schuman; Garrettson Ellis

[57] ABSTRACT

A device for suspension of a solution container in both an infusion and drain position, easily foldable or rollable for storage or carrying. The device comprises an elongated, flexible, foldable strap (10) attached at one end to a bracket (12), the bracket adapted to be secured to an elevated surface. There is an adjusting means, preferably a bolt (18) integral with the bracket to enable attachment and detachment of the bracket to an elevated surface. Finally, there are support means (24, 30) for suspension of the solution container, the support means being adjustably engagable with the strap at any desired location on the strap. Although primarily intended for use by patients practicing the medical procedure of continuous ambulatory peritoneal dialysis (CAPD), the device is readily usable for suspension of other container types.

5 Claims, 4 Drawing Figures

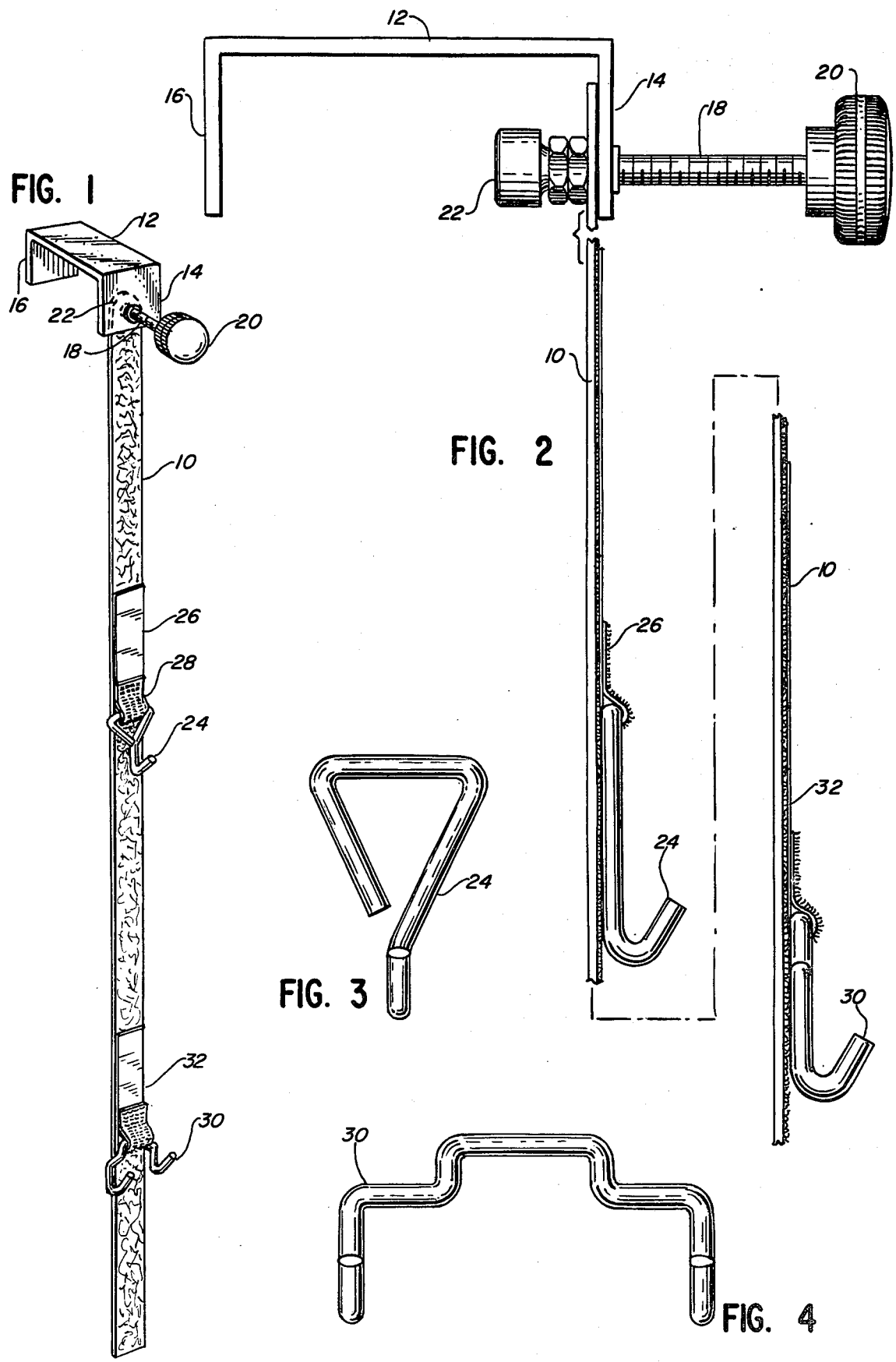

DEVICE FOR SUSPENSION OF A SOLUTION CONTAINER

BACKGROUND OF THE INVENTION

This invention relates to a device for suspension of a solution container, principally for use in conjunction with a peritoneal dialysis solution container.

Currently, the most widely used method of kidney dialysis for treatment of End Stage Renal Disease (ESRD) is "hemodialysis". Here, the patient's blood is cleansed by passing it through an artificial kidney in an artificial kidney dialysis machine. By the process of diffusion across a semipermeable membrane in the artificial kidney, impurities and toxins are removed from the patient's blood to thereby perform a natural function of the patient's kidneys. Hemodialysis is generally required three times a week, each dialysis requiring 4–5 hours in a dialysis center or at home. During dialysis, the patient is "tied" to the machine by venous and arterial blood lines which convey his blood to and from the artificial kidney.

Although used less frequently than hemodialysis, a procedure known as "intermittent peritoneal dialysis" (IPD) is an accepted method for treating ESRD. In this procedure, a dialysis solution is infused into the patient's peritoneal cavity by means of tubing and a catheter. The peritoneum, which defines the peritoneal cavity, contains many small blood vessels and capillary beds which act as a natural semipermeable membrane. This natural membrane may be contrasted with the artificial membrane used in hemodialysis. In both cases, however, impurities and toxins in the blood are removed by diffusion across a membrane—a cellulose membrane of an artificial kidney or a peritoneal membrane of a peritoneal cavity.

In intermittent peritoneal dialysis, dialysis solution remains in the patient's peritoneal cavity for a time sufficient for blood impurities to be removed by diffusion across the peritoneal membrane and into the dialysis solution. The impurity containing dialysis solution then is drained from the peritoneal cavity by means of a catheter and tubing, and a fresh supply of dialysis solution is infused. Intermittent peritoneal dialysis utilizes pumps or other auxillary equipment to which the patient is "tied" during dialysis; here also the patient must remain sedentary.

"Continuous ambulatory peritoneal dialysis" (CAPD) is another type of peritoneal dialysis which uses the peritoneum as a semipermeable membrane. The continuous procedure has the important advantage, however, of enabling the patient to be ambulatory and conduct a normal routine during dialysis. The patient is not "tied" to a machine, and he must be sedentary only for the time period required to drain and infuse dialysis solution from and into the peritoneal cavity. This infusion and draining is handled by tubing and a surgically implanted, indwelling catheter in the patient's abdominal wall and in communication with his peritoneal cavity.

CAPD is intended to be a patient self-care technique once the catheter is surgically implanted. Thus, it is important that the apparatus involved, e.g., tubing and solution container and ancillary equipment such as the present invention, be simple and easy to use. The present invention is intended to simplify the procedure for infusing and draining dialysis solution, the invention being useful in the home or other location as well as in a medical facility. The invention concerns a novel device for suspension of a solution container. The device is portable and may be attached to a door or other elevated surface for infusion and drainage of the dialysis solution. The invention is also easily folded or rolled for carrying or storage, and is primarily intended for use with plastic CAPD dialysis solution containers.

A support for surgical bags and drain tubes for attachment to the sides of hospital beds is disclosed in Garth U.S. Pat. No. 2,959,386. Here, a support fabricated from wire is attached to the side of a hospital bed for hanging a urinary drain bag to receive body effluent. Unlike the hanger disclosed in Garth, the present invention is suitable for other than a hospital environment and can be used in three modes: (1) infusion; (2) drain; and (3) storage or carrying.

A foldable leaf bag holder is shown in Ross U.S. Pat. No. 3,638,888 which supports a plastic bag in a vertical or horizontal position. The device in Ross is always utilized on the ground, unlike the present invention which is intended to be hung from a door, shelf, desk top, or other elevated surface for infusion and drain of solution. A butchering stand is disclosed in Duke U.S. Pat. No. 1,417,234, which is foldable for storage, but does not permit meat to be butchered in more than one position. The butchering stand is cumbersome and its and Ross' design would not be adaptable, as the present invention is, for support of a solution container in infusion and drain.

In pending U.S. patent application Ser. No. 093,356 of Kulin, et al., filed Nov. 13, 1979, commonly assigned, a solution container hanger constructed of wire is disclosed for support of a solution container in the infusion and drain positions. The hanger must be suspended from a door or other elevated surface during infusion, but is preferably placed on the floor for support of the solution container in the drain position. Although foldable for carrying or storage, the Kulin, et al. hanger cannot be "rolled" into the small size of the suspension device of this invention, and must be manually manipulated to go from an infusion to drain position.

None of the prior art hangers satisfy the following criteria for a device for suspension of a solution container adaptable for use in continuous ambulatory peritoneal dialysis: (1) able to be easily folded or rolled for storage and transportation in a size small enough to fit into a coat pocket, purse, or briefcase; and (2) able to be suspended from a height necessary for both infusion and drain of dialysis solution. Thus, there is a need to provide a device for suspension of a solution container which is easily portable and can be attached to an elevated structure for both infusion and drain. A device for suspension of a solution container which is simple in design is also desirable for ease of manufacture.

With the advent of dialysis solutions contained in plastic bags, and the development of continuous ambulatory peritoneal dialysis, a simple device for suspension of a solution container for use by patients in and outside of a hospital environment is desired. A simple, effective, inexpensive device is important, particularly from a patient self-care standpoint, when practicing CAPD. It is therefore, an object of this invention to provide a device for suspension of a solution container which is simple, effective, inexpensive, easily portable, and can be hung from any convenient structure for both infusion and drainage.

As will be fully explained below, the present invention is easy to operate. Ease of operation is important for the practice of CAPD because of the large number of patients with limited physical capacity because of poor eyesight, weakness, arthritis and the like. This invention also is particularly advantageous for use by children and geriatric patients for these same reasons.

SUMMARY OF THE INVENTION

The device for suspension of a solution container of the present invention comprises an elongated, flexible, foldable strap, preferably entirely fabricated of a VELCRO ® type material which can be easily rolled into a circular shape for easy storage and transportation. The device is small enough to be placed in a purse, brief case, or perhaps even a coat pocket. The strap has attached at one end a bracket, preferably a C-type bracket, more commonly referred to as a C-clamp, the bracket adapted to be secured to an elevated surface. There is adjusting means integral with the bracket, the adjusting means preferably being a bolt threadedly engaged through one side of the bracket which enables the bracket to be attached and detached conveniently from an elevated surface. Finally, there is support means, preferably a hook having a VELCRO type material strip integral with it so that the hook can be mated with the VELCRO strap, the hook able to be placed at any desired location on the strap so that one hook can potentially be used for suspension of a solution container both in the infusion and drain positions.

BRIEF DESCRIPTIONS OF THE DRAWINGS

Other objects, features and advantages of the present invention will become more fully apparent from the following detailed description of the preferred embodiment, the appended claims and the accompanying drawings in which:

FIG. 1 is a perspective view of the device for suspension of a solution container of the present invention;

FIG. 2 is a side view of the device;

FIG. 3 is a front view of a single hook which is the preferable design of a support means for suspension of a solution container in the infusion position; and FIG. 4 is a front view of a double hook support means which is the preferable design for suspension of a solution container in the drain position when practicing CAPD.

DETAILED DESCRIPTION OF THE PREFERRED EMBODIMENT

The preferred embodiment of the hanger of this invention is illustrated by way of example in FIGS. 1 and 2.

Referring to FIGS. 1 and 2, the present invention is shown in perspective in FIG. 1 and in side view in FIG. 2 with an elongated, flexible, foldable strap 10 attached at one end to a bracket 12, bracket 12 preferably a C-clamp design. The strap 10 is preferably six feet in length and one and a half inches in width and made from a VELCRO type material which can be folded, or preferably rolled, into a circular shape, for ease of storage and carrying. The bracket 12 has a preferable inside dimension between the sides 14 and 16 of one and three quarter inches which makes bracket 12 adaptable to fit the edges of most standard doors, tables, and chairs or other elevated surfaces.

The device has an adjusting means, preferably a bolt 18 threadedly engaged through side 14 of bracket 12. The bolt 18 has an adjusting knob 20 integral with one end of bolt 18, and exterior to bracket 12, and a pad 22 integral with the other end of bolt 18, pad 22 in the interior of bracket 12 between sides 14 and 16. As adjusting knob 20 is manually turned clockwise, bolt 18 threads through side 14 of bracket 12 and pad 22 moves to frictional contact with an elevated surface to secure bracket 12 to the elevated surface by means of the frictional contact of side 16 of bracket 12 and pad 22 with the elevated surface.

Adjustably engageable with strap 10 is a support means, preferably a single hook 24. Preferably, hook 24 has integral with it a VELCRO type material strip 26 which can be easily attached and detached from VELCRO type material strap 10. The preferable VELCRO type material of both strap 10 and strip 26 is VELCRO #80, which has a minimum straight shear strength of 6 pounds per square inch; this is adequate to support a typical plastic CAPD solution container filled with three liters of dialysis solution.

The strip 26 can be permanently integral with hook 24 by means of sonic welding or other securing methods at mating line 28 so that hook 24 will not undesirably detach from strip 26 when the full solution container is suspended from hook 24.

A plastic solution container which could be suspended from the device of this invention, and which is used extensively in CAPD, is marketed by Travenol Laboratories, Inc., of Deerfield, Illinois as an AMBU-FLEX ™ container. The AMBU-FLEX container has one hole on its hanger flap for positioning the container in an infusion position; the single hook 24 is a desirable design for the infusion support means. The AMBU-FLEX container has two holes on the flap on the end opposite the infusion flap, and therefore, it is preferable when the AMBU-FLEX container is used in conjunction with the present invention that a two hook design 30 be used as a support means for the AMBU-FLEX container in the drain position. However, a single hook 24 can be used for both infusion and drain.

Double hook support means 30 also has integral with it a VELCRO type material strip 32 which can be positioned anywhere on VELCRO type material strap 10.

A patient using the device of this invention for practicing CAPD could carry the entire device conveniently rolled up in a purse, brief case, or coat pocket. Hooks 24 and 30 and their corresponding strips 26 and 32 can be either carried by the patient attached to or detached from strap 10. When it is time for a CAPD exchange, the patient can remove the device from the convenient carrying place, and secure bracket 12 to an elevated surface, in most instances preferably the top of a door. Strap 10 can then be unrolled to hang its entire length from bracket 12.

If double hook 30 is used for draining, the patient can attach strip 32 to strap 10 at a location near enough the floor to permit drain of dialysis solution from the peritoneum into the solution container without the solution container contacting the floor. After draining, the patient can attach a fresh container of dialysis solution to his connection set leading to the catheter which communicates with his peritoneal cavity; the patient is now ready to infuse the fresh solution.

For infusion, the patient can attach strip 26, which is integral with hook 24, at a location high enough on strap 10 so that the fresh container of dialysis solution can be suspended from single hook 24 at a height sufficient to ensure an adequate flow rate of fresh dialysis solution into the peritoneal cavity.

Although the use of both single hook 24 and double hook 30 may be preferred by most patients, single hook 24 used for infusion and double hook 30 used for drain, the device is still operable with the use of one support means, either single hook 24 or double hook 30. The patient could first drain using hook 24 with integral strip 26 attached to strap 10 at a location low enough to permit adequate drain of solution. After draining and connecting a fresh container of dialysis solution, strip 26 with integral hook 24 can be detached from strap 10 and moved to a position high enough to permit an adequate infusion rate.

The foregoing methods have illustrated the primary advantages of this invention, that is, single positioning of bracket 12 on an elevated surface enables the patient to use strap 10 and the detachable support means, either hook 24 or double hook 30, for both drain and infusion; and the drain and infusion steps can be accomplished without repositioning the bracket 12, unlike any known solution container hanger, e.g., the solution container hanger disclosed in U.S. patent application Ser. No. 093,356 of Kulin, et al., filed Nov. 13, 1979, commonly assigned.

While the present invention has been disclosed in connection with the preferred embodiment thereof, it should be understood that there may be other embodiments which fall within the sphere and scope of this invention as defined by the following claims:

That which is claimed is:

1. A device for suspension of a solution container which comprises:
(a) an elongated, flexible, foldable strap;
(b) said strap attached at one end to a C-clamp type bracket, said bracket adapted to be secured to an elevated surface;
(c) adjusting means integral with said bracket to enable attachment and detachment of said bracket to said elevated surface; and
(d) hook means for suspension of said solution container, said support means adjustably engagable with said strap at any desired location on said strap said hook further comprising: a Velcro type material strip integral with said hook, said Velcro type material strip attachable and detachable from said strap, said strap made of a Velcro type material suitable to mate with said Velcro type material strip.

2. The device of claim 1, said adjusting means comprising:
a bolt threadedly engaged through one side of said bracket; said bracket a C-clamp type design.

3. The device of claim 2, said bolt further comprising:
an adjusting knob integral with one end of said bolt.

4. The device of claim 2, said bolt further comprising:
a pad integral with one end of said bolt for frictional attachment of said bracket to an elevated surface.

5. A device for suspension of a dialysis solution container which comprises:
(a) an elongated, flexible, foldable VELCRO type material strap;
(b) said strap attached at one end to a C-clamp type bracket, said bracket adapted to be secured to an elevated surface;
(c) a bolt engaged through one side of said bracket, said bolt enabling attachment and detachment of said bracket to said elevated surface; and
(d) a hook for support of said dialysis solution container, said hook adjustably engagable with said strap so that said hook can be placed at any desired location on said strap, said hook further comprising: a VELCRO type material strip integral with said hook, said VELCRO type material strip matingly engagable with said VELCRO type material strap.

* * * * *